United States Patent [19]

Mandal et al.

[11] Patent Number: 4,680,418
[45] Date of Patent: Jul. 14, 1987

[54] PROCESS FOR THE PRODUCTION OF A (1R,CIS)-4 ACETYL-6,6-DIMETHYL-3-OXABICYCLO-(3.1.0.)-HEX-2-ONE

[75] Inventors: Arun K. Mandal; Damodar G. Jawalkar; Satish W. Mahajan, all of Maharashtra, all of India

[73] Assignee: IEL Limited, Calcutta, India

[21] Appl. No.: 780,651

[22] Filed: Sep. 26, 1985

[30] Foreign Application Priority Data

Sep. 28, 1984 [GB] United Kingdom ............... 8424561

[51] Int. Cl.$^4$ .......................................... C07D 307/93
[52] U.S. Cl. ................................................ 549/305
[58] Field of Search ..................................... 549/305

[56] References Cited

U.S. PATENT DOCUMENTS 4,257,956  3/1981  Syrier ................................ 549/305
4,281,203  7/1981  Syrier ................................ 549/305

Primary Examiner—Jane T. Fan
Attorney, Agent, or Firm—Ladas & Parry

[57] ABSTRACT

A process for the production of (1R,Cis)-4-acetyl-6,6-dimethyl-3-oxabicyclo-(3.1.0.)-hex-2-one of the formula:

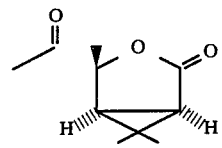

which involves reacting (1R,Cis)-4,7,7-trimethyl-3-oxabicyclo-(4.1.0.)-hept-4-en-2-one of the formula:

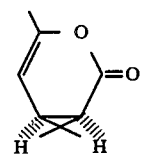

with bromine at a temperature of from 0° C. to 25° C. and treating the brominated reaction mixture at ambient temperature with water, an aqueous solvent solution or an aqueous base solution.

10 Claims, No Drawings

PROCESS FOR THE PRODUCTION OF A (1R,CIS)-4 ACETYL-6,6-DIMETHYL-3-OXABICYCLO-(3.1.0.)-HEX-2-ONE

The present invention relates in general to the field of pyrethroids which find special use as insecticides and which are remarkable for their low toxicity in mammals. More particularly, the present invention relates to a novel process for the production of (1R,Cis)-4-acetyl-6,6-dimethyl-3-oxabicyclo-(3.1.0.)-hex-2-one which is a useful intermediate in the preparation of cyclopropane carboxylate esters which are known to be active pyrethroids. In the description and claims which follow, this intermediate will for convenience be identified and referred to as (1R,Cis)-acetyl lactone.

(1R,Cis)-acetyl lactone can be represented by the following formula:

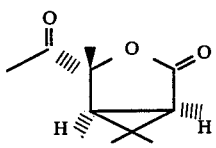

The importance of (1R,Cis)-acetyl lactone of the formula given above lies in the fact that it constitutes a convenient starting material for the manufacture of (1R,Cis)-acid of the general formula:

wherein X is chlorine or bromine and R is hydrogen. The (1R,Cis)-acid can in turn be converted to the corresponding (1R,Cis)-pyrethroid esters and one important class of these pyrethroid esters can be represented by the general formula:

wherein X is chlorine or bromine and R is

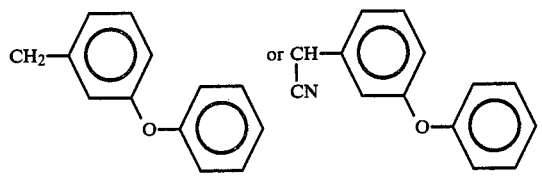

It has been established that for the pyrethroids to evince maximum insecticidal activity, the acid portion of the esters should have the (1R,Cis) configuration.

The only known process in the prior art for the production of the intermediate (1R,Cis)-acetyl lactone is the one described in British Patent No. 2052479. According to this British patent, (1R,Cis)-4,7,7-trimethyl-3-oxabicyclo-(4.1.0.)-hept-4-en-2-one of the formula:

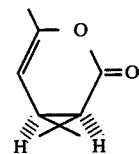

is reacted with one or more peracids such as m-chloroperbenzoic acid. Unfortunately, the peracids employed as reagent apart from being expensive also pose potential hazards when employed in large scale operations.

It is therefore the object of the present invention to avoid the drawbacks and disadvantages of the prior art and to provide a novel one-step process which apart from being less expensive to work avoids the employment of hazardous reagents such as peracids.

The present invention accordingly provides a process for the production of (1R,Cis)-4-acetyl-6,6-dimethyl-3-oxabicyclo(3.1.0.)-hex-2-one of the formula:

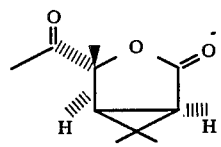

which comprises reacting (1R,Cis)-4,7,7-trimethyl-3-oxabicyclo(4.1.0.)-hept-4-en-2-one of the formula:

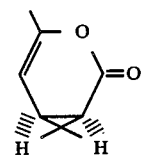

with a halogen at a temperature of from 0° C. to 25° C. and treating the halogenated reaction mixture at ambient temperature with water, an aqueous solvent solution or an aqueous base solution.

The starting compound (1R,Cis)-4,7,7-trimethyl-3-oxabicyclo(4.1.0.)-hept-4-en-2-one can be obtained from (1R,Cis)-2,2-dimethyl-3-(2-oxopropyl)-cyclopropane-1-carboxylic acid of the formula:

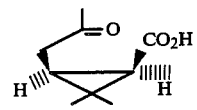

(disclosed in U.S. patent application Ser. No. 566652 by A. K. Mandal et al. and in Indian Patent No. 294/Cal/83) by employing any known means, for instance the method of U.S. Pat. No. 4132717.

Conveniently, the halogenation reaction is effected in the presence of a solvent which is preferably a chlorinated hydrocarbon solvent having a dielectric constant between 2 and 12. The solvent most preferred for the halogenation reaction is carbon tetrachloride which is employed at a concentration of halogen of from 0.25M to 3.0M, preferably 2.0M.

The halogen best employed for the reaction has been found to be bromine while the temperature range most preferred for halogenation is from 0° C. to 5° C.

The aqueous solvent solution which may be employed for the aqueous treatment of the halogenated reaction mixture can comprise a solution of water and an etheral solvent having a dielectric constant in the range of from 2 to 5. Preferred etheral solvents are tetrahydrofuran and dioxane.

Preferred bases for the aqueous base solution include carbonates and hydrogen carbonates of alkali metals of which the one most preferred is sodium hydrogen carbonate.

As stated, the aqueous treatment of the halogenated reaction mixture is effected at ambient temperature with a temperature of from 20° C. to 30° C. being particularly convenient.

The process of the present invention, which possesses the advantages of less expense and the absence of hazards over the prior art, produces the desired (1R,Cis)-acetyl lactone in excellent yield. This lactone lends itself admirably as an intermediate in the production of (1R,Cis)-acid which in turn is convertible to the corresponding pyrethroids. One convenient method of employing the intermediate lactone to produce (1R,Cis)-acid comprises reacting the lactone with a peracid such as m-chloroperbenzoic acid to produce (1R,Cis)-acetoxy lactone of the formula:

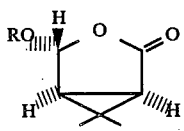

wherein R is

hydrolysing the acetoxy lactone with a base to produce (1R,Cis)-lactol having the same general formula but wherein R is hydrogen and then converting the lactol to (1R,Cis)-acid of the formula shown above by employing procedure analogous to that described in German Patent No. 2827627.

The invention will now be illustrated in greater detail in the following non-limitative examples in each of which the identity and purity of the product were confirmed by spectroscopic and/or GLC analysis.

EXAMPLE 1

(−)-(1R,Cis)-4-acetyl-6,6-dimethyl-3-oxabicyclo-(3.1.0.)-hex-2-one

To a solution of 15.2 g (0.1 mole) of (1R,Cis)-4,7,7-trimethyl-3-oxabicyclo-(4.1.0.)-hept-4-en-2-one [$(\alpha)_D^{25}$ −100° C., C 1, CHCl$_3$] in 30 ml of carbon tetrachloride at 0°–5° C. there were added dropwise with stirring 16 g (5.0 ml, 0.1 mole) of bromine in 25 ml of carbon tetrachloride. 50 ml water were added and the reaction mixture was stirred at 25° C. for 12 hours. The organic layer was separated and washed once with saturated aqueous sodium carbonate solution and dried over anhydrous sodium sulphate. Removal of carbon tetrachloride yielded 13.5 g (80%) of the desired product as a white microcrystalline solid which was further re-crystallised from ether as needles, m.p. 64° to 65° C., $(\alpha)_D^{25}$ −48.5° C., (C 1.0, EtOH).

EXAMPLE 2

(−)-(1R,Cis)-4-acetyl-6,6-dimethyl-3-oxabicyclo-(3.1.0.)-hex-2-one

To a solution of 15.2 g (0.1 mole) of (1R,Cis)-4,7,7-trimethyl-3-oxabicyclo-(4.1.0.)-hept-4-en-2-one [$(\alpha)_D^{25}$ −100° C., C 1 CHCl$_3$] in 30 ml of carbon tetrachloride at 0.5° C. there was added a solution of 16.0 g (5.0 ml, 0.1 mole) of bromine in 20 ml of carbon tetrachloride. The reaction mixture was treated with 60 ml of a 1:1 mixture of tetrahydrofuran and water and stirred at 25° C. for from 8 to 10 hours. The organic layer was washed once with saturated aqueous sodium bicarbonate solution and dried. The removal of the solvent yielded 14.3 g (85%) of the desired product as a white microcrystalline powder. Re-crystallisation was effected from ether, m.p. 64° to 65° C., $(\alpha)_D^{25}$ −48.6° C., (C 1.0, EtOH).

EXAMPLE 3

(−)-(1R,Cis)-4-acetyl-6,6-dimethyl-3-oxabicyclo-(3.1.0)-hex-2-one

To a solution of 15.2 g (0.1 mole) of (1R,Cis)-4,7,7-trimethyl-3-oxabicyclo-(4.1.0.)hept-4-en-2-one [$(\alpha)_D^{25}$ −100° C., C 1, CHCl$_3$] in 30 ml of carbon tetrachloride, there were added 16 g (0.1 mole) of bromine in 20 ml of carbon tetrachloride. The reaction mixture was stirred with saturated aqueous sodium bicarbonate solution for 4 hours. The organic layer was dried and the solvent removed to yield 13.9 g (82%) of the desired product as crystalline powder which was thereafter re-crystallised from ether, m.p. 64° to 65° C., $(\alpha)_D^{25}$ −48.46° C. (C 2.0, EtOH).

We claim:

1. A process for the production of (1R,Cis)-4-acetyl-6,6-dimethyl-3-oxabicyclo-(3.1.0)-hex-2-one of the formula:

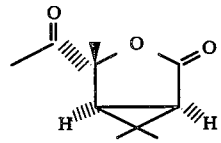

which comprises reacting (1R,Cis)-4,7,7-trimethyl-3-oxabicyclo(4.1.0.)-hept-4-en-2-one of the formula:

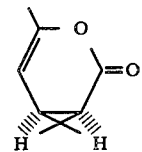

with bromine at a temperature of from 0° C. to 25° C. and treating the brominated reaction mixture at ambient temperature with water, an aqueous solvent solution or an aqueous base solution.

2. A process as claimed in claim 1 wherein said bromination reaction is effected in the presence of a solvent.

3. A process as claimed in claim 2 wherein said solvent is a chlorinated hydrocarbon solvent having a dielectric constant between 2 and 12.

4. A process as claimed in claim 2 wherein said solvent is carbon tetrachloride.

5. A process as claimed in claim 1 wherein said bromination is effected at a temperature of from 0° C. to 5° C.

6. A process as claimed in claim 1 wherein said aqueous solvent solution comprises a solution of water and one or more etheral solvents having a dielectric constant in the range of from 2 to 5.

7. A process as claimed in claim 6 wherein said etheral solvent is selected from tetrahydrofuran, dioxane and mixtures thereof.

8. A process as claimed in claim 1 wherein the base in said aqueous base solution is selected from carbonates and hydrogen carbonates of alkali metals.

9. A process as claimed in claim 8 wherein said base is sodium hydrogen carbonate.

10. A process as claimed in claim 1 wherein said aqueous treatment of said brominated reaction mixture is effected at a temperatured of from 20° C. to 30° C.

* * * * *